(12) United States Patent
Divins et al.

(10) Patent No.: US 8,420,844 B2
(45) Date of Patent: Apr. 16, 2013

(54) HYDROSILYLATION PROCESS FOR GASEOUS UNSATURATED HYDROCARBONS

(75) Inventors: Larry A. Divins, Parkersburg, WV (US); Frank D. Mendicino, Marietta, OH (US); John P. Smith, Friendly, WV (US); Marco Veri, Vito (IT)

(73) Assignee: Momentive Performance Materials Inc., Waterford, NY (US)

( * ) Notice: Subject to any disclaimer, the term of this patent is extended or adjusted under 35 U.S.C. 154(b) by 678 days.

(21) Appl. No.: 12/459,315

(22) Filed: Jun. 30, 2009

(65) Prior Publication Data

US 2010/0004476 A1 Jan. 7, 2010

Related U.S. Application Data

(60) Provisional application No. 61/077,196, filed on Jul. 1, 2008.

(51) Int. Cl.
*C07F 7/04* (2006.01)
*C07F 7/00* (2006.01)
*C07F 7/08* (2006.01)

(52) U.S. Cl.
USPC ............ 556/478; 556/450; 556/465; 556/487

(58) Field of Classification Search .................. None
See application file for complete search history.

(56) References Cited

U.S. PATENT DOCUMENTS

| | | | |
|---|---|---|---|
| 3,404,169 A | 10/1968 | Henri et al. | |
| 3,793,358 A | 2/1974 | Bauer et al. | |
| 4,138,440 A * | 2/1979 | Chang et al. | 585/402 |
| 4,276,426 A | 6/1981 | Lindner et al. | |
| 4,579,965 A | 4/1986 | Kanner et al. | |
| 4,898,961 A | 2/1990 | Baile et al. | |
| 5,041,595 A | 8/1991 | Yang et al. | |
| 5,929,269 A | 7/1999 | Steding | |
| 6,410,772 B2 * | 6/2002 | Okuyama et al. | 556/479 |
| 6,414,176 B2 | 7/2002 | Preiss et al. | |
| 6,472,549 B1 | 10/2002 | Batz-Sohn et al. | |
| 6,897,280 B2 * | 5/2005 | Heisler et al. | 528/15 |
| 7,005,532 B2 | 2/2006 | Suzuki et al. | |
| 7,145,028 B2 | 12/2006 | Geisberger et al. | |
| 8,039,646 B2 * | 10/2011 | Bade et al. | 549/215 |
| 2005/0027138 A1 | 2/2005 | Janeiro et al. | |
| 2005/0272862 A1 * | 12/2005 | Ochs et al. | 524/591 |
| 2010/0184935 A1 * | 7/2010 | Oberhellman et al. | 528/15 |

FOREIGN PATENT DOCUMENTS

EP 1059119 A2 12/2000

* cited by examiner

*Primary Examiner* — Porfirio Nazario Gonzalez
*Assistant Examiner* — James Meadows
(74) *Attorney, Agent, or Firm* — Dominick G. Vicari; Joseph S. Ostroff

(57) ABSTRACT

Organosilicon compounds are prepared by the addition reaction of a gaseous unsaturated hydrocarbon with a silane or siloxane containing at least one silicon-bonded hydrogen atom in the presence of a hydrosilylation catalyst in a liquid reaction medium. In this process the unsaturated hydrocarbon and optionally the silane or siloxane is dispersed into the liquid reaction medium by a jet eductor (also known as a venturi pump) device and the resultant gas-in-liquid dispersion is introduced into a bubble reactor.

20 Claims, 1 Drawing Sheet

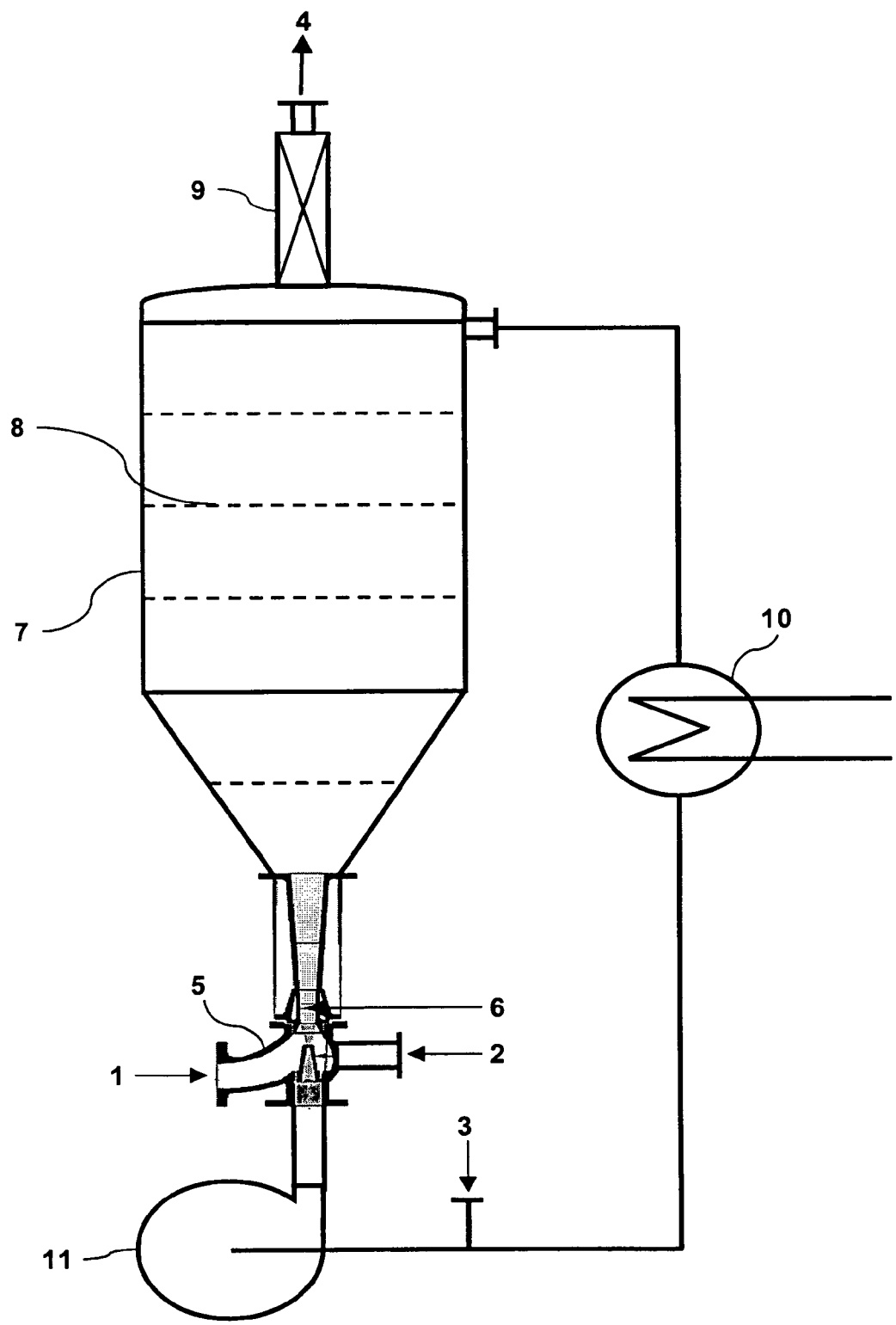

HYDROSILYLATION PROCESS FOR GASEOUS UNSATURATED HYDROCARBONS

CROSS-REFERENCE TO RELATED APPLICATIONS

This application claims priority to U.S. application No. 61/077,196 filed Jul. 1, 2008, which is herein incorporated by reference in its entirety.

FIELD OF THE INVENTION

This invention relates to a hydrosilylation method for the preparation of organosilicon compounds. More particularly, this invention relates to the addition reaction of gaseous unsaturated hydrocarbons with a silane or siloxane containing at least one silicon-bonded hydrogen atom in the presence of a hydrosilylation catalyst.

BACKGROUND OF THE INVENTION

Organosilicon compounds may be prepared in general by the addition reaction of unsaturated hydrocarbons with Si—H containing silanes or siloxanes. For example, Walter Noll describes in *Chemistry and Technology of Silicones*, Second Edition (1968), Pages 49-55, the addition reaction for silanes and siloxanes. This type of addition reaction to hydrocarbons containing carbon-carbon multiple bonds is termed hydrosilylation. Heat, light, radiation, or catalysts may initiate hydrosilylation reactions. Catalysts may be noble metals, bases, or peroxides. Noble metals, especially platinum, are usually preferred. The form of catalyst may be homogeneous or heterogeneous.

Hydrosilylation reactions utilizing unsaturated hydrocarbons that are gaseous at reaction conditions have had reported deficiencies related to incomplete reactions, slow batch reaction rates to avoid loss of the hydrocarbon, and formation of secondary (disilylalkane) byproducts in the case of alkenylsilanes, wherein the disilylalkanes correspond to the primary alkenylsilane products.

For example, U.S. Pat. No. 3,404,169 discloses the preparation of vinylhalosilanes by the reaction of acetylene with a halo-hydrogensilane at atmospheric pressure and moderate temperature in a liquid aromatic diluent in the presence of a platinum catalyst. The '169 patent discloses that reactants are introduced in a premixed form through a single tube, which dips to the bottom of the reactor and ends in a sintered glass cylinder having pores. In apparent recognition of poor mixing at the tube exit, the '169 patent discloses that an agitating device may be advantageous to homogenize the reaction mass and avoid local over-heating. Reported patent example product selectivity calculated on the amount of feed silane consumed were 83%, 86% and 91% for three examples of methylvinyldichlorosilane preparation, 81% for dimethylvinylchlorosilane, and 87% and 91% for vinyltrichlorosilane. The yield losses were predominantly to disilylethane byproducts.

U.S. Pat. No. 3,793,358 discloses that an alkenylsilane may be prepared by reacting acetylene or substituted acetylene with a silane having at least one silicon bonded hydrogen atom in the presence of an addition catalyst and disilylethane at a temperature from about 120° C. to about 220° C. at a pressure from about 0.1 to about 5 atmospheres gauge, and the resulting alkenylsilane is removed continuously as a gas from the reaction space at the rate at which it is formed. Examples of the '358 patent provide that reactants are introduced at 0.4 atmospheres gauge pressure in a premixed form below a perforated plate into the lower end of a reaction tower containing disilylalkane and platinum catalyst. This pressure is generally considered a safe condition for the use of acetylene. Acetylene decomposition is known to occur at pressures above 15 psig or approximately 1 atmosphere gauge. No additional mixing in the reaction tower is disclosed. In the Examples of the '358 patent, product selectivity calculated on the amount of feed silane consumed were 87% and 88% for methylvinyldichlorosilane, 92% and 95% for vinyltrichlorosilane, and a reported 74% product concentration for dimethylvinylchlorosilane. The yield losses were predominantly to disilylethane byproducts.

U.S. Pat. No. 4,276,426 discloses a process for preparing organosilicon compounds by the continuous introduction of a halosilane, dihalosilane, or disiloxane having Si-bonded hydrogen, a compound containing an aliphatic multiple bond, and a catalyst to a pipe shaped reactor, where the reaction mixture is maintained in a liquid phase and is being continuously removed from the reactor, wherein the reaction mixture is circulated in the reactor at a rate of at least 1,000 cm per minute. According to the patent examples, the reaction is conducted from about 120° C. to about 170° C. at a pressure of approximately 6 bar. Although this pressure is above the "safe" pressure for acetylene, the reactor inside diameter is limited to 20 mm, which is less than the detonation propagation limit. Unless many such pipe reactors are combined into a complex multi-pipe unit, this reactor diameter limit severely restricts the production capacity that could be obtained and hence it is not commercially practical.

U.S. Pat. No. 4,579,965 discloses the preparation of vinyl tri(tertiary-substituted) alkoxysilanes by reacting a tri-t-alkoxysilane with an alkyne in the presence of a platinum hydrosilylation catalyst at a reaction temperature greater than 150° C. The reaction is conducted at the alkenyl gas inlet pressure, which is greater than atmospheric. The reaction is conducted in an autoclave with a batch time from about 1 to 3 hours with a large excess of acetylene. Product selectivity was reported to be greater than 90% for tertiary alkoxysilane. For primary and secondary alkoxysilanes, the selectivity was poor. Therefore the process of the '965 patent has a narrow practical application, as most vinylsilanes of commercial interest are primary silanes.

U.S. Pat. No. 4,898,961 discloses the continuous preparation of alkenylsilanes whereby a gaseous mixture of acetylenic hydrocarbon and a silane containing a silicon-bonded hydrogen atom is directed into contact with a reaction medium containing a hydrosilylation catalyst and in the form of a thin liquid layer or film. According to the '961 patent, the reaction medium is preferably the product of the reaction or can optionally be a solvent, and the reaction is conducted below the decomposition pressure of the acetylenic hydrocarbon (less than 2 atmospheres) and in the temperature range of 50° C. to 80° C. The form of the reactor is a vertical tube reactor wherein the liquid medium flows as a layer or film within the tubes and the exterior of the tubes is water-cooled. The liquid reaction medium is introduced to the upper end of the tubes through a distributor weir to direct the flow along the tube walls. The gaseous mixture is introduced through nozzles to the bottom of the tubes. The '961 patent examples disclose the effect of using a solvent that has greater solubility for acetylene and reports that dimethyl ether of ethylene glycol is more effective than methylethyl ketone, which in turn is more effective than xylene.

Product selectivity for methylvinyldichlorosilane ranged from about 93% when using xylene to about 95% when using dimethyl ether of ethylene glycol. U.S. Pat. No. 5,041,595 discloses a batch or continuous method for producing high purity vinylalkoxysilanes by gradually feeding an alkoxysilane containing low levels of ionic chloride or alkyl amine into a reaction zone containing an alkyne and a platinum hydrosilylation catalyst. The '595 patent discloses that the total concentration of ionic chloride and alkyl amines (measured as nitrogen) contaminants is maintained below 0.1 weight percent and most preferably below 0.005 weight percent, which minimizes the formation of tetraalkoxysilane and alkylalkoxysilane byproducts. The reaction zone is operated at less than 75 psia and preferably less than 25 psia and at a temperature between about 50° C. and about 150° C. The reaction medium is vinylalkoxysilane product or disilylalkoxyalkane or a solvent selected from cumene, toluene, xylene, and o-dichlorobenzene and may optionally contain a reaction promoter selected from the group consisting of phenothiazine, diphenylmethane, diphenylamine, and carboxylic acids promoter.

The '595 patent discloses that good mixing is important in the process of the invention. A stirred reactor was used for the patent example experiments. Patent example product selectivity calculated on the amount of feed silane consumed for the preparation of vinyltrimethoxysilane in o-dichlorobenzene solvent were about 92% at atmospheric pressure and about 96% at a pressure of 7-12.7 psig. When the reaction medium was vinyltrimethoxysilane product, the product selectivity was 87% at a reaction pressure of 7 psig and when the reaction medium was disilyltrimethoxyethane, the product selectivity was 89% at atmospheric pressure. Product selectivity for a methylvinyidimethoxysilane preparation example was 96% at 12.3 psig and in o-dichlorobenzene solvent.

U.S. Pat. No. 6,414,176 discloses the preparation of vinylsilanes by reacting silanes with a liquid phase at superatmospheric pressure containing acetylenic hydrocarbon and a hydrosilylation catalyst. The spent actylenic hydrocarbon is replenished during the reaction while maintaining a constant pressure. Silane is added to the liquid phase, which already contains the acetylenic hydrocarbon and catalyst. The effect of maintaining a constant concentration of acetylenic hydrocarbon throughout the reaction is that the reaction is conducted at high molar excess of the acetylenic hydrocarbon. The '176 patent discloses that the reaction is preferably conducted in an inert high boiling solvent, selected from aliphatic and aromatic hydrocarbons, and that high boiling aromatic hydrocarbons are particularly preferred. The '176 patent discloses that the reaction is preferably conducted at a low temperature of from 40° C. to about 50° C. and at a pressure of 15 to 20 bar, which is well above the generally considered safe pressure of 15 psig, the pressure where acetylene decomposition can begin. The reaction yield for vinyltrimethoxysilane was disclosed in an example as 99%.

U.S. Pat. No. 7,005,532 discloses the batch or continuous preparation of organoalkoxysilanes by hydrosilylating an organosilicon compound having at least one hydrogen-silicon bond and at least one alkoxy group and an organic compound having a carbon-carbon unsaturated bond in vapor phase in the presence of a mixture containing a hydrosilylation catalyst and a polyalkylene glycol and supported on an inert carrier. The '532 patent discloses that the process is conducted at a preferred temperature range of 100-180° C. and at a preferred pressure of 1-5 MPa (10-50 Bar), and always less than 10 MPa (100 Bar), which are all well above the generally considered safe pressure of 1 bar gauge, the pressure where acetylene decomposition can occur. Indicated reactor types are vibrating bed, moving bed, fixed bed, or fluidized bed. Product selectivity for vinyltrimethoxysilane was 94%, 94%, and 97% for the three patent examples, but reaction yield was 67%, 51%, and 83% for the same examples because of relatively low conversion of the feed trimethoxysilane. Product selectivity for vinyltrichlorosilane was 85% and reaction yield was 52%.

It would be desirable to devise an improved method for the preparation of organohalosilanes, organoalkoxysilanes, and organosiloxanes from gaseous unsaturated hydrocarbons at high product selectivity and in high conversion yield. It would be also particularly desirable to prepare dimethylvinylchlorosilane in high yield.

SUMMARY OF THE INVENTION

The present invention relates to a batch or continuous process for producing organosilanes, organohalosilanes, organoalkoxysilanes, and organosiloxanes by hydrosilylating gaseous unsaturated hydrocarbons. The process comprises the following steps:

(A) feeding an unsaturated gaseous hydrocarbon (Reagent A) to an intensively mixed reaction zone composed of a jet eductor (aka venturi pump) device and associated piping and feeding a silane (Reagent B) and/or siloxane (Reagent C) containing at least one silicon-bonded hydrogen atom to the same reaction zone wherein Reagent A and Reagent B and/or Reagent C are contacted with a high flow rate liquid reaction medium containing a hydrosilylation catalyst and a solvent to form a gas-in-liquid dispersion and to initiate a hydrosilylation reaction, (B) conducting the gas-in-liquid dispersion to a plug flow gas bubble reaction zone for completion of the hydrosilylation reaction to form an organosilicon product and for removal of the heat of reaction by cooling devices, and (C) recovering said hydrosilation reaction product from said plug flow gas bubble reaction zone.

In an embodiment of the invention, a feed molar ratio for gaseous hydrocarbon to silane or siloxane of greater than 1 per silicon-bonded hydrogen atom site on the silane or siloxane is maintained.

The present invention is directed at improvements in mixing and reacting gaseous unsaturated hydrocarbons with liquid or gaseous silanes or siloxanes in a liquid reaction medium containing a hydrosilylation catalyst. The method has the features of a first intensive mixing and reaction zone of the jet eductor or venturi pump type for the reactants to create a gas-in-liquid dispersion within the reaction medium and a second close-coupled plug flow reaction zone of the bubble reactor type for high conversion yield. The reaction medium comprises a dispersed or solubilized hydrosilylaton catalyst and a liquid phase. The liquid phase is selected from the group consisting of the organosilicon product of the reaction, hydrocarbon solvent, siloxane fluid, or in the case of acetylenic hydrocarbon reactants, the disilylalkane byproduct. The organosilicon product of the reaction may be removed from the reaction space as a gas or liquid phase.

The process of this invention has the advantages of low pressure, hence less hazardous operation when acetylene is utilized, and excellent mixing of reactants with the reaction medium without the use of devices that may provide ignition sources. Furthermore, the process of this invention can produce a wider array of products than previously known methods.

BRIEF DESCRIPTION OF THE DRAWINGS/FIGURES

FIG. 1 illustrates one embodiment of an integrated jet eductor (also known as a venturi pump) and bubble reactor system for the hydrosilylation of gaseous hydrocarbons with halosilanes, alkoxysilanes, or siloxanes.

DETAILED DESCRIPTION OF THE INVENTION

The invention relates to an efficient and direct method for producing organosilanes, organohalosilanes, organoalkoxysilanes, and organosiloxanes by hydrosilylating gaseous unsaturated hydrocarbons. The method comprises:

(A) feeding an unsaturated gaseous hydrocarbon (Reagent A) to a reaction zone having a jet eductor and feeding a silane (Reagent B) and/or siloxane (Reagent C) containing at least one silicon-bonded hydrogen atom to the same reaction zone wherein the reactants are contacted with a high flow rate liquid reaction medium containing a hydrosilylation catalyst and a solvent to form a gas-in-liquid dispersion and to initiate a hydrosilylation reaction, (B) conducting the gas-in-liquid dispersion to a plug flow gas bubble reaction zone for completion of the hydrosilylation reaction to form hydrosilation reaction product, and (C) recovering said hydrosilation reaction product from the plug flow gas bubble reaction zone.

In an embodiment of the present invention a feed molar ratio for Reagent A to Reagent B or Reagent C or mixture of reagent B and Reagent C of greater than 1 per silicon-bonded hydrogen atom site on the Reagent B or Reagent C is maintained.

Reagent A in the method of this invention can be any unsaturated hydrocarbon which will hydrosilylate and which is gaseous at the hydrosilylation reaction conditions. Generally these hydrocarbons are terminally unsaturated alkenes (or olefins) and alkynes including halogenated alkenes and alkynes. The preferred alkenes have 1-8 carbon atoms. Alkene examples include ethylene, propylene, 1-butene, butadiene, methyl-1-butene, 1-pentene, 1-hexene, 1-heptene, 1-octene, 1,1,1-trifluoropropene, 1,1-difluoroethylene, and 1-chloro-1-fluoroethylene. The preferred alkynes have 1-8 carbon atoms. Alkyne examples include acetylene, propyne, 1-butyne, 1-pentyne, 1-hexyne, and 1-octyne.

Reagent B is a silane, halosilane or an alkoxysilane containing at least one silicon-bonded hydrogen atom. Suitable silanes, halosilanes or alkoxysilanes include those of the general formula:

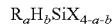
$$R_aH_bSiX_{4-a-b}$$

where R represents a monovalent hydrocarbon radical or substituted monovalent hydrocarbon radical and has 1 to 6 carbon atoms; X represents a halogen or an alkoxy group containing from 1 to 4 carbon atoms; b is 1 or 2; a is 0, 1, 2, or 3; and (a+b) is 4 or less. Silanes that can be used include, but are not limited to, trimethoxysilane, triethoxysilane, methyldimethoxysilane, trichlorosilane, methyldichlorosilane, dimethylchlorosilane, trimethylsilane and mixtures thereof. Certain contaminants in alkoxysilanes are preferably minimized to avoid yield losses. For example, the total concentration of alkyl amines (measured as nitrogen) and ionic chloride contaminants preferably should not exceed about 0.10 weight percent in aggregate or individually in the alkoxysilane.

Reagent C is a siloxane or disiloxane containing at least one silicon-bonded hydrogen atom, which has an acceptable viscosity for hydrosilylation in a bubble reactor. Suitable siloxanes include those of the general formula:

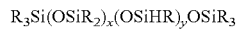
$$R_3Si(OSiR_2)_x(OSiHR)_yOSiR_3$$

Suitable disiloxanes include those of the general formula:

$$HR_2SiOSiR_2H$$

where for siloxanes and disiloxanes, R is an alkyl radical or substituted hydrocarbon group containing 1 to 18 carbon atoms or is an aryl group, x is less than 20, and y is 5 or less. Suitable siloxanes and disiloxanes include, but are not limited, to heptamethyltrisiloxane and tetramethyldisiloxane.

The catalyst used in the process is a hydrosilylation catalyst. Many such catalysts are known in the art and any of them that are dispersible or soluble in the liquid reaction medium can be used to promote the reaction. Homogeneous catalysts are preferred, but heterogeneous catalysts that are dispersible in the reaction medium are acceptable. Known hydrosilylation catalysts include the elements or compounds of platinum, rhodium, ruthenium, palladium, iridium, cobalt, copper, nickel, iron, tin, and titanium. Specific examples include chloroplatinic acid, complexes of chloroplatinic acid, platinum-olefin complexes, platinum-vinyl siloxane complexes, platinum-amine complexes, and platinum-phosphine complexes. Known promoters of homogeneous hydrosilylation reactions may be co-employed. Examples include phenothiazine, diphenylmethane, diphenylamine, and carboxylic acids.

The solvent used in the process principally forms the reaction medium and in which the hydrosilylation catalyst is dispersed or solubilized. Because the hydrosilylation reaction occurs in the liquid phase, the solvent must function to transfer and solubilize gaseous and liquid reactants into the liquid phase. A more effective solvent will improve reaction rate and yield. See, for example, U.S. Pat. No. 4,898,961, which is incorporated herein by reference, which discloses that the dimethyl ether of ethylene glycol is a more effective solvent for acetylene than methylethyl ketone, which in turn is a more effective solvent than xylene.

It is known that ethers, acetones, and acetates are more effective solvents for acetylene than aromatics. For example, acetylene solubility data is reported as part of the IUPAC-NIST Solubility Data Series, which was compiled and published by Peter G. T. Fogg in the Journal of Physical Chemistry Reference Data, Vol. 30, No. 6, (2002). This reference includes solubility data for one silane, poly(vinyltrimethyl silane), $(C_5H_{12}Si)_n$. Measurements of the solubility of acetylene in vinyltrimethoxysilane found it equivalent or better than most ethers, acetone, and acetates, and when compared to some other materials found it has the following relationship: acetylene solubility in disilyltrimethoxysilane>vinyltrimethoxysilane>hexane>dichlorobenzene.

Siloxanes are also known to have excellent gas solubility. Preferred silane and siloxane solvents for the reaction medium are the product of the said hydrosilylation reaction, the disilylalkane byproduct from acetylenic hydrosilylations, and siloxane fluids, e.g. dimethyl and cyclic siloxanes.

The choice of solvent to be utilized may additionally depend of the method of product recovery. If product recovery is by vaporization directly from the reaction medium in the bubble reactor, the solvent must have a higher boiling point than the hydrosilylation product. If product recovery is by separation external of the bubble reactor, the solvent boiling point may be less or greater than the hydrosilylation product, depending on the separation technique.

The hydrosilylation reaction may be run continuously or in a batch mode. Based on economic and safety considerations, continuous operation is preferred. The following description of the process assumes the preferred continuous operation.

In an embodiment of an integrated reactor system for conducting the hydrosilylation reaction of the process of the invention, the reaction is first conducted in an intensive mixing zone formed by a jet eductor (also known as a venturi pump) and is secondly conducted in a plug flow bubble reaction zone directly connected to the intensive mixing zone. Because the kinetics of the subject hydrosilylation reactions tends to be fast, the reaction is rate limited by the mass transfer from the gas phase to the liquid phase. The intensive jet eductor mixing zone provides excellent mass transfer from the gas phase to the liquid reaction medium and a significant portion of the overall conversion occurs in this first reaction zone. The plug flow nature of the bubble reactor then takes the reaction to high conversion completion by providing sufficient residence time to complete the reaction.

To illustrate the process, reference is made to FIG. 1.

Gaseous unsaturated hydrocarbon (1) is passed into a jet eductor mixing zone (6) through the low pressure entrance or suction of the eductor (5). This low pressure gas feed capability allows the hydrocarbon to be conducted to the reactor without the use of compression. This is particularly advantageous for maintaining acetylene below its potential decomposition pressure of 15 psig.

The motive force for providing the gas suction is the pumping (11) of the reaction medium at high flow rate through the jet eductor nozzle. The silane or siloxane compound (2) having at least one Si—H group is preferably added to the jet eductor through a second dual feed port. A dual feed jet eductor provides the best mixing of gas and liquid feeds without pre-reactions, which may potentially occur at other feed points. For example, it is easy to feed a liquid silane or siloxane to the suction side of the reaction medium pump, e.g. at feed point (3). However, when the silane or siloxane is fed at this location, it is likely to react with hydrocarbon gas saturated in the recirculating reaction medium and the resulting stoichiometry is not ideal for high product yield.

When acetylenic compounds are used as the hydrocarbon, the concentration of reactants in the recirculating reaction medium favor the formation of the undesirable disilylalkane byproduct. If the silane or siloxane is relatively low boiling, it is feasible to premix vaporized silane or siloxane with the hydrocarbon gas prior to the eductor suction. This has the advantage of good reactant mixing, but the potential disadvantage of backflow into the hydrocarbon source. To maximize the conversion of the silane or siloxane compound and particularly to minimize the formation of disilylalkane when using acetylenic hydrocarbons, the unsaturated hydrocarbon should be used in a molar ratio of greater than 1.0 per silicon-bonded hydrogen atom site on the silane or siloxane molecule.

Hydrosilylation catalyst may be added to the inlet side (3) of the reaction medium pump or may be added elsewhere in the reaction system, e.g. to the bubble reactor. It is not critical where the catalyst is added because it is long lasting in the reaction system and will be well-mixed in the reaction medium. It is also not critical if the catalyst is added continuously or batch-wise. The hydrosilylation catalyst is used in a quantity sufficient to catalyze the reaction. Catalyst concentrations in the range of 1 to 500 ppm by weight based on the weight of reactants and reaction medium are generally acceptable. Preferably, because of the expense of a catalyst, the concentrations are typically maintained lower in the range of 1 to 50 ppm and often below 10 ppm. The process of the invention has the potential for extremely low catalyst usage when the reaction medium is not the hydrosilylation product and the product is vaporized directly from the bubble reactor.

The gas-in-liquid dispersion of the reactants, reaction medium, and catalyst passes from the discharge of the jet eductor directly into the bubble reactor (7). The bubble reactor is sized to provide sufficient residence time to complete the hydrosilylation reaction. The bubble reactor may be designed to operate in a bubbly flow regime and to avoid slug flow or turbulent flow. It is known that maintaining gas velocities below 5 cm/s typically assures bubbly flow. The bubble reactor may optionally include perforated plates (8) or other types of distributors to suppress bubble coalescence and to distribute the gas phase radially.

The hydrosilylation reaction is exothermic. A high flow rate of the liquid reaction medium through the jet eductor carries released heat of reaction to the bubble reactor. The bubble reactor may be directly cooled (typically an external cooling jacket or internal cooling coils) to remove the heat of reaction or cooling may be accomplished by cooling the recirculating reaction medium. To improve the safety of the reaction system when reacting flammable and potentially decomposable gasses, e.g. acetylene, it is preferred that the bubble reactor be operated liquid full. To more safely separate gas from the liquid phase, a separation device (9) containing little open space may be advantageous at the top of the bubble reactor. The liquid reaction medium exits the bubble reactor and may be passed through a heat exchanger (10) to remove the heat of reaction.

Product may be recovered in at least two ways. One method is to run the reactor system at a temperature sufficient to vaporize the product (4) directly from the bubble reactor. This method has several advantages: high product purity from distilling off the product, recycle of catalyst, and utilization of the hydrocarbon saturated in the reaction medium. A second method is to run the reactor at a temperature sufficiently below the product boiling point to avoid appreciable product vaporization and to take the product off the reactor as liquid mixed with the reaction medium. This has an advantage of running the reactor at a lower temperature, which improves hydrocarbon solubility in the reaction medium and minimizes decomposition reactions, but requires an additional (distillation) step to remove the product from the reaction medium and results in the loss of hydrocarbon saturated in the reaction medium.

In an embodiment of the invention, wherein the reaction system is run with product vaporization directly from the bubble reactor, the reaction system is operated in the temperature range from about 120° C. to about 180° C., suitably from about 125° C. to about 160° C. In this mode of operation, the reaction medium should have a boiling point above about 190° C. For the production of products from acetylenic hydrocarbons, disilylalkane may be advantageously used as it is a byproduct of those reactions. For the production of products from olefinic hydrocarbons, a high boiling point inert solvent such as low viscosity dimethyl siloxane fluids or the cyclic D5 pentamer siloxane may be utilized or another high boiling hydrocarbon solvent such as an ether of diethylene glycol or a high boiling alkane may be utilized. In the mode of running the reaction system with product recovery in a separate separation step, the reaction system is operated in the temperature range from about 50° C. to about 130° C., suitably in the range from about 80° C. to about 120° C.

A major advantage of the process of this invention is the capability to feed the gaseous unsaturated hydrocarbon reactant at low pressure and to likewise run the reaction system at low pressure. When using acetylenic hydrocarbons, safety is improved by running the system below 15 psig. But the low pressure gaseous hydrocarbon feed capability does not limit the reaction system pressure. The reaction system has the advantage that it may be operated at any pressure achievable by the jet eductor and it is known that higher pressure improves the gaseous hydrocarbon solubility in the reaction medium. When using olefinic hydrocarbons as a hydrosilylation reactant, the reaction system pressure may be elevated to 10 atmospheres or more.

This invention is further disclosed by means of the following examples. It is understood, however, that the invention is not limited solely to the particular Examples given below.

EXAMPLES

Examples 1-12

Continuous reactions (Examples 1-9) between acetylene and a halosilane or alkoxysilane were conducted in a laboratory scale version of a bubble reactor. The reactor was a 1-inch diameter by 24-inch tall glass tube filled approximately 75% with ¼ inch Berl ceramic saddle random packing. To control the bubble reactor temperature, the tube was wrapped with electric heat tape in two zones and thermocouples were installed in the inlet (bottom) and outlet (top) of the reactor. The bottom thermocouple controlled the bottom heat tape zone and the top thermocouple controlled the upper heat tape zone of the reactor. Acetylene was fed from a cylinder at approximately 15 psig and passed through purification and drying mediums and then through a flowmeter before being premixed with silane. Silane was pressure fed from a 125 ml pressure addition funnel into the acetylene gas stream. The premixed reactants were then fed into the bottom of the bubble reactor. The outlet of the bubble reactor was equipped with a back-pressure valve and pressure gauge and was connected by tubing to a dry ice condenser.

Before operation, the bubble reactor was filled with solvent containing a platinum catalyst, which was chloroplatinic acid dissolved in ethanol for all examples in Table 1. The solvent for Examples 1-9 was octamethylcyclotetrasiloxane, otherwise known as tetramer or $D_4$. At startup, the reactor was thoroughly purged with nitrogen and heated to the desired reaction temperature prior to the initiation of acetylene flow. After the acetylene flow was stable, silane flow was started. Acetylene flow for all tests was about 14 liters/hr at 15 psig, which is sufficient to assure stoichiometric excess at all the tested silane flows. Silane reactant feed was conducted at three flow rates during the tests: 25 ml/hr, 50 ml/hr, and 100 ml/hr. During operation the lab reactor was run at 11 psig. Product was evaporated from the solvent and collected from the dry ice condenser. Runs were made with four silanes: (1.) trichlorosilane (TCS) to produce vinyltrichlorosilane product, (2.) methyldichlorosilane (MH) to produce methylvinyldichlorosilane product, (3.) dimethylchlorosilane ($M_2H$) to produce dimethylvinylchlorosilane product, and (4.) trimethoxysilane (TMS) to produce vinyltrimethoxysilane. The trichlorosilane runs averaged 92.6% vinyltrichlorosilane and 4.2% disilylethane by calibrated gas chromatography of undistilled product. The methyldichlorosilane runs averaged 94.4% methylvinyldichlorosilane and 3.6% disilylethane. The dimethylchlorosilane runs averaged 89.1% dimethylvinylchlorosilane and 9.3% disilylethane. The trimethoxysilane runs averaged 86.2% vinyltrimethoxysilane and 9.4% disilylethane. The results of these tests are summarized in Table 1 (Examples 1-9).

Examples 10-12 were run in a lab experimental apparatus similar to that of Examples 1-9 except that the reactor is 1-inch diameter by 40-inch tall glass tube. The operating conditions and procedure were essentially the same as described above. The major difference lies in the solvent used in the reactions. Example 10 used a mixture of the disilylethanes of vinyltrichlorosilane and methylvinyldichlorosilane as the solvent. Example 11 used disilylethane of dimethylvinylchlorosilane as solvent.

Example 12 demonstrates the hydrosilylation reaction between heptamethyltrisiloxane (MD'M) and ethylene. This reaction used the product MD*M as solvent, wherein superscript*indicates a Si-bonded ethyl group.

TABLE 1

| Ex. | Reactant | Reaction Temperature | Reactant Flow Rate | CPA Catalyst Concentration | Product Wt. % | Disilylethane Wt. % |
|---|---|---|---|---|---|---|
| 1 | TCS | 125° C. | 13.1 g/hr/cm² | 80 ppm | 94.32 | 2.17 |
| 2 | TCS | 145° C. | 26.2 g/hr/cm² | 80 ppm | 90.83 | 6.22 |
| 3 | MH | 125° C. | 10.8 g/hr/cm² | 40 ppm | 95.34 | 3.48 |
| 4 | MH | 126° C. | 10.8 g/hr/cm² | 80 ppm | 93.47 | 3.67 |
| 5 | M₂H | 124° C. | 8.6 g/hr/cm² | 40 ppm | 85.98 | 11.40 |
| 6 | M₂H | 125° C. | 17.1 g/hr/cm² | 20 ppm | 92.37 | 6.28 |
| 7 | M₂H | 126° C. | 8.6 g/hr/cm² | 20 ppm | 88.90 | 10.31 |
| 8 | TMS | 124° C. | 9.4 g/hr/cm² | 40 ppm | 84.43 | 10.70 |
| 9 | TMS | 125° C. | 4.7 g/hr/cm² | 40 ppm | 87.92 | 8.10 |
| 10 | MH | 128° C. | 9.9 g/hr/cm² | 50 ppm | 90.40 | 7.40 |
| 11 | M₂H | 125° C. | 6.3 g/hr/cm² | 50 ppm | 91.00 | 6.70 |
| 12 | MD'M | 120° C. | 8.3 g/hr/cm² | 20 ppm | 94.28 | N/A |

Compared to previously known acetylenic hydrosilylations conducted at relatively low and hence safer pressures, the vinyltrichlorosilane, vinyltrimethoxysilane, and methylvinyldichlorosilane yields were similar to previous processes, but the dimethylvinylchlorosilane runs exceeded the product selectivity performance of previous processes.

Examples 13-15

Because it was difficult to build and conduct experiments at laboratory scale for the integrated jet eductor and bubble reactor system of the process of this invention, the laboratory scale tests of Examples 1-12 were conducted in only the bubble reactor part of the system with premixed acetylene and silane reactants. However, it was more amenable to conduct integrated jet eductor and bubble reactor system tests at larger scale. The data in Table 2 originates from these larger scale tests for Examples 13-15.

Typical of larger scale experiments, the tests were run for hours and many data points were collected. Table 2 presents an average of each entire test run. The tests were conducted at 1.2 bar gauge pressure (17.6 psig). The reaction medium was crude (undistilled) vinyltrimethoxysilane product and catalyst. The catalyst was chloroplatinic acid in the concentration range of 5-10 ppm platinum. Acetylene was in the range of 5 to 10 mole percent excess. Trimethoxysilane conversion to crude product exceeded 98 percent.

TABLE 2

| Reac. Ex. | Reactant | Reaction Temperature | Reactant Flow Rate | Silane Feed Point | Product Wt. % | Disilylethane Wt. % |
|---|---|---|---|---|---|---|
| 13 | TMS | 120° C. | 15 g/hr/cm² | Pump Suction | 93.4 | 5.7 |
| 14 | TMS | 120° C. | 36 g/hr/cm² | Pump Suction | 88.4 | 10.6 |
| 15 | TMS | 120° C. | 36 g/hr/cm² | Eductor | 92.5 | 6.5 |

The data in Table 2 demonstrate that the product selectivity of vinylsilane relative to disilylethane improves in an integrated jet eductor and bubble reactor system compared to a bubble reactor. For example, the TMS flow rate of the Example 8 laboratory scale bubble reactor compares relatively with the TMS flow rate of the larger scale integrated reactor system of Example 13, yet the integrated system has an improvement of about 9 percentage points in product selectivity. Examples 14 and 15 demonstrate the effect of co-feeding the trimethoxysilane to the ideal stoichiometry of the jet eductor rather than to the non-ideal stoichiometry in the suction side of the recirculation pump. There is a difference of about 4 percentage points in improved product selectivity through this better silane feed point. Furthermore, the integrated jet eductor and bubble reactor system demonstrated an excellent conversion of feed silane to product.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A batch or continuous process for producing organosilanes, organohalosilanes, organoalkoxysilanes, and/or organosiloxanes by hydrosilylating gaseous unsaturated hydrocarbons, which comprises:
    (a) feeding unsaturated gaseous hydrocarbon (Reagent A) to a reaction zone having a jet eductor and feeding silane (Reagent B) and/or siloxane (Reagent C) containing at least one silicon-bonded hydrogen atom to said reaction zone wherein said Reagent A and said Reagent B and/or Reagent C are contacted with a liquid reaction medium containing a hydrosilylation catalyst and a solvent wherein said liquid reaction medium is pumped through the jet educator nozzle to form a gas-in-liquid dispersion with said Reagent A and said Reagent B and/or Reagent C and to initiate a hydrosilylation reaction,
    (b) conducting the gas-in-liquid dispersion to a plug flow gas bubble reaction zone and maintaining gas velocities below 5 centimeters per second for completion of the hydrosilylation reaction to form a hydrosilation reaction product; and
    (c) recovering said hydrosilation reaction product from said plug flow gas bubble reaction zone.

2. The process of claim 1, wherein said Reagent A is terminally unsaturated alkene, halogenated alkene of 1-8 carbon atoms or a mixture thereof.

3. The process of claim 2, wherein the terminally unsaturated alkene is selected from the group consisting of ethylene, propylene, 1-butene, butadiene, methyl-1-butene, 1-pentene, 1-hexene, 1-heptene, and 1-octene, and the halogenated alkene is selected from the group consisting of 1,1,1-trifluoropropene, 1,1-difluoroethylene, and 1-chloro-I-fluoroethylene.

4. The process of claim 1, wherein Reagent A is terminally unsaturated alkyne, halogenated alkyne of 1-8 carbon atoms or mixture thereof.

5. The process of claim 4, wherein the terminally unsaturated alkyne is selected from the group consisting of acetylene, propyne, 1-butyne, 1-pentyne, 1-hexyne, and 1-octyne and the halogenated alkyne is selected from the group consisting of 3-chloropropyne and 3-chloro-1-butyne.

6. The process of claim 1, wherein Reagent B possesses the general formula:

$$R_aH_bSiX_{4-a-b}$$

where R represents a monovalent hydrocarbon radical or substituted monovalent hydrocarbon radical and has 1 to 6 carbon atoms; X represents a halogen or an alkoxy group containing from 1 to 4 carbon atoms; b is 1 or 2; a is 0, 1, 2, or 3; and (a+b) is 1, 2, 3 or 4.

7. The process of claim 6, wherein Reagent B is selected from the group consisting of trimethoxysilane, triethoxysilane, methyldimethoxysilane, trichlorosilane, methyldichlorosilane, dimethylchlorosilane, trimethylsilane, and mixtures thereof.

8. The process of claim 1, wherein Reagent C is selected from the group consisting of siloxane of the general formula $$R_3Si(OSiR_2)_x(OSiHR)_yOSiR_3,$$

disiloxane of the general formula:

$$HR_2SiOSiR_2H,$$

and mixtures thereof wherein in each formula, R is independently substituted or unsubstituted hydrocarbon group containing 1 to 18 carbon atoms, x is less than 20 and y is 5 or less, but not less than 1.

9. The process of claim 8, wherein Reagent C is selected from the group consisting of heptamethyltrisiloxane, tetramethyldisiloxane and a mixture thereof.

10. The process of claim 1, further including a promoter.

11. The process of claim 1, wherein the solvent is selected from the group consisting of the hydrosilylation reaction product, siloxane fluid, organosiloxane fluid, alkane, ether of ethylene glycol, ether of diethylene glycol, ether of triethylene glycol, ether of tetraethylene glycol, ether of propylene glycol, cumene, toluene, xylene, o-dichlorobenzene, and mixtures thereof.

12. The process of claim 11, wherein the hydrosilylation reaction product is vinylchlorosilane, vinylalkoxysilane, bis(chlorosilyl)alkane, bis(alkoxysilyl)alkane or mixtures thereof.

13. The process of claim 11, wherein the siloxane fluid solvent is selected from the group consisting of linear dimethylsiloxane and cyclic polydimethylsiloxane, and the alkane is selected from the group consisting of heptane, n-octane, n-nonane, n-decane, n-undecane, n-dodecane, and mixtures thereof.

14. The process of claim 1, wherein the silane or siloxane is a liquid or gas premixed with the gaseous hydrocarbon before feeding to the jet eductor reaction zone.

15. The process of claim 1, wherein the silane or siloxane is a liquid or gas premixed with the reaction medium prior to introduction to the jet eductor reaction zone.

16. The process of claim 1, wherein the reaction is carried out at a temperature between about 120° C. and about 180° C.

17. The process of claim 1, wherein the reaction is carried out at a temperature between about 50° C. and about 130° C.

18. The process of claim 1, wherein said reaction zone is at a pressure of less than about 41 atmospheres gauge (600 psig).

19. The process of claim 1, wherein the hydrosilylation reaction product is removed from the reaction zone as a gas or a liquid or mixture thereof.

20. The process of claim 1, wherein a feed molar ratio for Reagent A to Reagent B or Reagent C or mixture of Reagent B and Reagent C of greater than 1 per silicon-bonded hydrogen atom site on said Reagent B or Reagent C is maintained.

\* \* \* \* \*